United States Patent
Aksela et al.

(10) Patent No.: US 6,590,120 B1
(45) Date of Patent: Jul. 8, 2003

(54) METHODS FOR THE PREPARATION OF AN N-BIS-[2-(1,2-DICARBOXY-ETHOXY)-ETHYL] AMINE DERIVATIVE AND PRODUCTS OF THE METHODS AND THEIR USES

(75) Inventors: Reijo Aksela, Espoo (FI); Ilkka Renvall, Espoo (FI); Aarto Paren, Vaasa (FI)

(73) Assignee: Kemira Chemicals Oy, Helsinki (FI)

( * ) Notice: Subject to any disclaimer, the term of this patent is extended or adjusted under 35 U.S.C. 154(b) by 0 days.

(21) Appl. No.: 09/623,727

(22) PCT Filed: Mar. 8, 1999

(86) PCT No.: PCT/FI99/00180

§ 371 (c)(1),
(2), (4) Date: Sep. 8, 2000

(87) PCT Pub. No.: WO99/46234

PCT Pub. Date: Sep. 16, 1999

(30) Foreign Application Priority Data

Mar. 9, 1998 (FI) .................................................. 980530

(51) Int. Cl.[7] .............................................. C07C 229/00
(52) U.S. Cl. ...................................... 560/171; 562/568
(58) Field of Search ............................ 562/568; 566/171

(56) References Cited

U.S. PATENT DOCUMENTS 5,907,055 A * 5/1999 Greindl et al.
6,093,849 A * 7/2000 Aksela et al.

FOREIGN PATENT DOCUMENTS

| DE | 19502294 A1 | 8/1996 |
|---|---|---|
| JP | 6-282044 | 10/1994 |
| JP | 7-120894 | 5/1995 |
| JP | 7-120899 | 5/1995 |
| JP | 7-261355 | 10/1995 |
| WO | WO 97/45586 | 12/1977 |
| WO | WO 96/22964 | 8/1996 |
| WO | WO 97/30207 | 8/1997 |
| WO | WO 97/30208 | 8/1997 |
| WO | WO 97/30209 | 8/1997 |
| WO | WO 97/30210 | 8/1997 |
| WO | WO 97/45396 | 12/1997 |
| WO | WO 97/45585 | 12/1997 |
| WO | WO 99/25919 | 5/1999 |

OTHER PUBLICATIONS

Ossipova et al. Issled. Khim. Redk.Soputstv. Elem. 1966, 170–4 Russian conference English abstract only provided. From STN Search of Chemical Abstracts.*

Jakara, J. et al., "Peracetic Acid in Low AOX and High Brightness Pulp Production," *Kami Pa Gikyoshi* 52:4, pp. 485–492, 1998.

van Westrenen, J. et al., "The synthesis of polyhydroxycarboxylates, Part 6. N–Alkylation of amino compounds by a Michael–type addition with maleate," *Recl. Trav. Chim. Pays–Bas 109*, pp. 474–478, 1990.

* cited by examiner

Primary Examiner—Samuel Barts
Assistant Examiner—Paul A. Zucker
(74) Attorney, Agent, or Firm—Pennie & Edmonds LLP

(57) ABSTRACT

Methods for the preparation of an N-alkyl-N-bis-(2-(1,2-dicarboxy-ethoxy)-ethyl)-amine derivative are described, products of the methods as well as uses of the products. The derivative is prepared by reacting an alkali or earth alkali metal salt of maleic acid with an N-substituted diethanolamine, the reaction taking place with the two ethanol groups of the diamine while the substituent group bound to the N atom remains unaffected, or alternatively by first reacting diethanolamine with an alkali or earth alkali metal salt of maleic acid to yield N-bis-(2-(1,2-dicarboxy-ethoxy)-ethyl)-amine, which is then reacted with a substitution reagent to obtain the final product. The derivative is useful as chelating agents, e.g., in the bleaching of chemical or mechanical pulp or in textile bleaches containing hydrogen peroxide or a peracid, or as a calcium binder in detergents and cleaning agents.

29 Claims, No Drawings

METHODS FOR THE PREPARATION OF AN N-BIS-[2-(1,2-DICARBOXY-ETHOXY)-ETHYL] AMINE DERIVATIVE AND PRODUCTS OF THE METHODS AND THEIR USES

This application is a 371 of PCT/FI99/00180 filed Mar. 8, 1999.

FIELD OF THE INVENTION

The invention relates to methods for the preparation of N-bis-[2-(1,2-dicarboxy-ethoxy)-ethyl]-amine derivative, and to the products of the method, and to the uses of those products.

The general formula I of the compounds that can be prepared according to the invention is

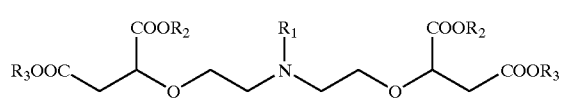

(I)

where $R_1$ is:
- an alkyl hydrocarbon chain containing 1–30-carbon atoms,
- an alkyl hydrocarbon chain containing 1–30 carbon atoms as well as 1–10 carboxylic acid groups attached to said chain, or alkali or earth alkali metal salt thereof,
- an alkyl hydrocarbon chain containing 1–30 carbon atoms and 1–10 carboxylic acid esters attached to said chain,
- a polyethoxylated hydrocarbon chain containing 1–20 ethoxyl groups,
- a carboxylic acid amide containing 1–30 carbon atoms, where N—$R_1$ bond is an amide bond, or
- an N-alkyl-N-bis-[2-(1,2-dicarboxy-ethoxy-(ethyl]-amine containing 1–20 carbon atoms in the alkyl chain, or an alkali or earth alkali metal salt thereof, and $R_2$ and $R_3$ are: hydrogen, an alkali metal ion or an earth alkali metal ion or an alkyl group containing 1–30 carbon atoms.

The compounds to be prepared find use especially as chelating agents.

BACKGROUND OF THE INVENTION

Transition metal ions and earth-alkali metal ions are bound as water-soluble chelates, for example, in various washing processes. Chelates of metal ions are used in photography chemicals in the developing processes.

When oxygen or peroxide compounds are used in the total chlorine free (TCF) bleaching of pulp it is important to remove the transition metals from the fiber before bleaching, since transition metal ions catalyze the decomposition of peroxy compounds, thus forming radical compounds. In consequence of these reactions the strength properties of the fiber are deteriorated.

Peroxy compounds such as hydrogen peroxide and peroxy acids can also be used in the so-called ECF-bleaching (elemental-chlorine-free-bleaching). Also in sequences which use chlorine dioxide or a combination of chlorine dioxide and peroxy acids, as described in the application FI-974221, a chelating agent can advantageously be used. Traditionally chelating agents are used in the alkaline peroxide bleaching of mechanical pulps such as SGW (stone groundwood), TMP (thermomechanical pulp), PGW (pressure groundwood), CTMP (chemi-theromechanical pulp), etc. A chelating agent can be used directly in the bleaching or as a pretreatment before the bleaching proper. This is especially the case when a multistage peroxide bleaching is employed.

At present, the complexing agents most commonly used in the applications mentioned above are ethylenediaminetetraacetic acid (EDTA) and its salts and di-ethylenetriaminepentaacetic acid (DTPA) and its salts. These are excellent complexing agents, but their biodegradability is poor.

Patent applications FI-960758, FI-960757, FI-960756 and FI-960755 disclose the use of aspartic acid derivatives as chelators in the bleaching of pulp. Such chelators include ethylenediaminedisuccinic acid (EDDS) and its alkali and earth-alkali metal salts, as well as iminodisuccinic acid (ISA) and its alkali and earth-alkali metal salts. EDDS and ISA are effective chelators of transition metals. In addition, they are biodegradable.

EDDS-type aspartic acid derivatives with longer hydrocarbon chain than in EDDS, are known from JP patent applications 7 261 355 and 6 282 044. One such substance is N,N'-(oxide-2,1-ethanediyl)-bis-L-aspartic acid.

In most cases the chelators are disposed to waste waters after their use. In order to minimize the nitrogen load in waste waters the nitrogen contents of the chelator should be as low as possible. Biodegradable chelators of the type EDDS, wherein some of the nitrogen atoms have been replaced with oxygen atoms, are disclosed in JP patent applications 7 120899 and 7 120894. The applications disclose the use of various isomers of N-[2-(1,2-dicarboxyethoxy)-ethyl]-aspartic acid (EDODS) in photographic chemicals. A method to prepare EDODS by $La^{3+}$-catalyzed O-alkylation of maleic acid salts has been described in the literature (J. van Vestrenen et al., Recd. Trav. Chem. Pays. Bas., vol. 109, 1990, p. 474–478).

However, in working tests performed by the applicants, EDODS did not prove to be a sufficiently effective chelator in pulp and paper applications. One possible explanation for the poor chelation result is the length of the carbon chain between the dicarboxyl ethoxy ethyl groups. If the carbon chain is not sufficiently long, strains are produced in the molecule during complexing and the metal complex will not be sufficiently stable.

SUMMARY OF THE INVENTION

In a previous application WO97/45396 by the present applicant there were disclosed compounds according to the formula II.

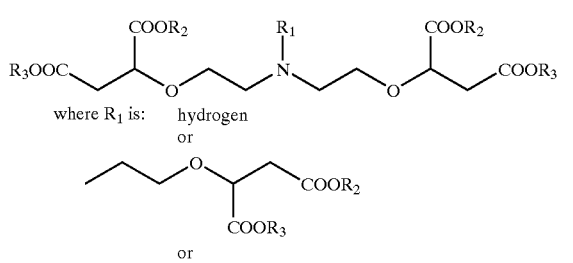

II where $R_1$ is: hydrogen
or

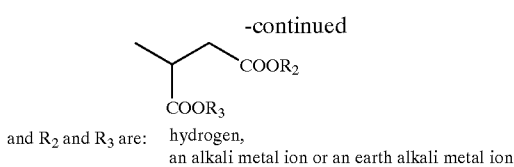

and R₂ and R₃ are: hydrogen,
an alkali metal ion or an earth alkali metal ion

These compounds include N-bis-[2-(1,2-dicarboxy-ethoxy)-ethyl]-amine (BCEEA), N-tris-[2-(1,2-dicarboxy-ethoxy)-ethyl]-amine (TCEEA) and N-bis-[2-(1,2-dicarboxy-ethoxy)-ethyl]-aspartic acid (BCEEAA), as well as the alkali metal and earth alkali metal salts of the said compounds, preferably $Na^+$, $K^+$, $Ca^{2+}$ and $Mg^{2+}$ salts.

In the molecular structure of said compounds, the central atom is a secondary or tertiary nitrogen atom and additionally, the molecule contains four or six carboxylic acid groups, which coordinate effectively with transition metal ions. The carbon chains are sufficiently long in terms of the formation of advantageous bond angles.

The object of the present invention is to provide methods for the preparation of effective chelating agents which would be biodegradable and contain a minimum amount of nitrogen.

According to the invention compounds of the formula (I) can be prepared according to the method where an alkali or earth alkali metal salt of maleic acid is brought to a reaction with an N-substituted diethanolamine with a substituent group $R_1$, to react with the two ethanol groups of said diethanolamine while the substituent group $R_1$ bound to the N atom is essentially unreactive with said maleic acid salt and thus preserved in the derivative obtained as a product, and optionally further reacting the product with a substitution agent, for example 2-bromoacetic acid or 2-chloroacetic acid to obtain a second product. With the exception of the compound referred to as BCEEAA in the above the compounds of the formula (1) are new compounds.

The invention thus comprises preparation of amine compounds according to the formula (I) by using alkali metal or earth-alkali metal salts of maleic acid and N-substituted diethanolamines as starting material in the presence of a lanthanide or earth alkali metal catalyst, in accordance with the following reaction.

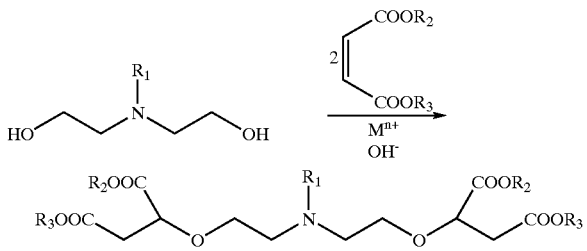

where $R_1$ has a meaning as defined above in connection with the formula (I)
and $R_2$ and $R_3$ alkyl, alkali or earth alkali metal ions.

The preferred meanings of $R_1$ are alkyl and $(CH_2)_n COOR$, where n=1–20 and R=alkyl, alkali or earth alkali metal.

The maleic acid salt which is the intermediate stage in the synthesis can be prepared in an aqueous solution by preferably using, available initial substances such as maleic anhydride and alkali metal or earth alkali metal compounds. Alkali metal compounds suitable for the reaction include lithium hydroxide, sodium hydroxide, potassium hydroxide, sodium carbonate, potassium carbonate, and lithium carbonate. Earth alkali metal compounds suitable for the reaction include magnesium hydroxide, magnesium oxide, magnesium carbonate, calcium oxide, calcium hydroxide, and calcium carbonate.

The formation of maleate is an exothermal reaction. When maleic anhydride is added to water, maleic acid is formed. When an alkali is added to this solution at a suitable rate, the temperature of the reaction mixture will increase to 80–90° C., which is a temperature preferable for the performing of the alkylation reaction.

The amino alcohol, which is a diethanol amine derivative, and the lanthanum compound used as the catalyst can thereafter be added rapidly to the alkaline reaction mixture.

Alternatively, the amino alcohol can be added to the reaction mixture at pH 7 and the pH is adjusted alkaline thereafter.

Rare earth metal ions or their mixtures can be used as the catalyst. Rare earth metal compounds containing organic ligands, achiral or chiral, can be used as catalyst. Likewise, suitable catalysts for O-alkylation include earth-alkali metal compounds such as calcium oxide, calcium hydroxide, calcium carbonate, magnesium oxide, magnesium hydroxide and magnesium carbonate. Furthermore, nickel compounds can be used as the catalyst.

Rare earth metal catalyzed O-alkylation of maleic acid salt with amino alcohols is a useful reaction, since the synthesis is a one-pot synthesis and the catalyst can be recycled. The catalyst can be separated from the reaction mixture after the reaction by rendering the reaction mixture acidic by means of mineral acids or organic acids followed by addition of oxalic acid to the reaction mixture. The rare earth metal oxalate precipitate formed can be separated from the reaction mixture by filtration. The catalyst can also be precipitated from the reaction mixture by addition of a molar excess of oxalic acid. Furthermore, the catalyst can be precipitated from the reaction mixture by addition of sodium carbonate. The rare earth metal carbonate formed can be separated from the reaction mixture by filtration.

The pH of the reaction mixture before the precipitation of the catalyst can be adjusted by using hydrochloric acid, sulfuric acid, nitric acid, phosphoric acid, formic acid, acetic acid or oxalic acid, most preferably hydrochloric acid, formic acid, acetic acid or oxalic acid.

It is preferable to use as the catalyst lanthanum(III) compounds, such as lanthanum maleate, lanthanum(III) nitrate, lanthanum(III) chloride, lanthanum oxide or lanthanum octanoate. Likewise, lanthanum compounds which contain organic ligands, chiral ligands or achiral ligands, can be used as a catalyst in the reaction. Also other metal salts belonging to the lanthanum group can advantageously be used, especially such as praseodymium and neodymium salts depending on the availability and price of the compounds.

The lanthanum(III) ion used as a catalyst can be separated from the oxalate precipitate by treating the precipitate with nitric acid or hydrochloric acid. After the treatment the catalyst can be reused. Moreover, the lanthanum ions can be recovered to lanthanum oxide ($La_2O_3$), lanthanum hydroxide or lanthanum carbonate by treating the precipitate at elevated temperatures (400–1000° C.).

When the lanthanum catalyst is precipitated from the reaction mixture as lanthanum carbonate, it can be either reused as is or converted to lanthanum oxide ($La_2O_3$) or lanthanum hydroxide by treating the precipitate at elevated temperatures (400–1000° C.).

The invention further comprises a modification of the above described process in which an alkali metal or earth-alkali metal salt of maleic acid and diethanolamine are used as starting materials in the presence of a lanthanide or earth alkali metal catalyst. The synthesis starts with the following reaction:

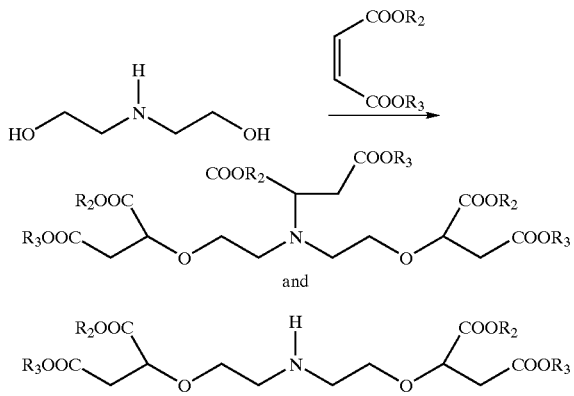

where $R_2$ and $R_3$=alkyl, alkali or earth alkali metal ions.

N-bis-[2-(1,2-dicarboxy-ethoxy)-ethyl]-aspartic acid (BCEEAA) as obtained can be converted to N-bis-[2-(1,2-dicarboxy-ethoxy)-ethyl]-amine by stirring the acidic reaction product containing N-bis-[2-(1,2-dicarboxy-ethoxy)-ethyl]-aspartic acid BCEEAA at elevated temperature for 1–2 hours. The cyclic amide A formed in this reaction can be further converted to N-bis-[2-(1,2-dicarboxy-ethoxy)-ethyl]-amine BCEEA in basic conditions. These reactions are as follows:

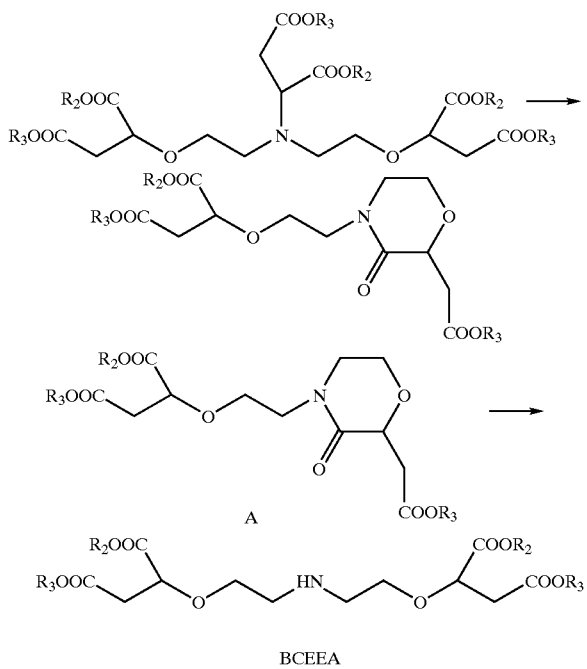

At the last stage of the process the N-bis[2-(1,2-dicarboxy-ethoxy)-ethyl]-amine as obtained is N-substituted by using a substitution agent replacing the hydrogen bound to the N atom with an organic group. The N-bis[2-(1,2-dicarboxyethoxy)-ethyl]-amine can thus be N-substituted by using a carboxylic acid halide, a carboxylic acid anhydride, a methoxylalcoxyl halide or an alkyl halide. 2-chloroacetic acid and 2-bromoacetic acid may be cited as examples. If for instance an organic chloride is used as the substitution agent the reaction is as follows:

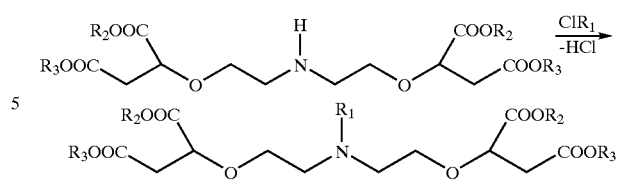

$R_1$ may have the meanings as defined before.

The invention specifically comprises the novel compounds according to formula (I) wherein $R_1$ is a group selected from alkyl groups and groups comprising an alkyl chain with a single carboxylic acid group, and $R_2$ and $R_3$ represent hydrogen or alkali or earth alkali metal ions. N-methyl-N-bis-[2-(1,2-dicarboxy-ethoxy)-ethyl]-amine or its alkali or earth alkali metal salt and N-carboxymethyl-N-bis-[2-(1,2-dicarboxy-ethoxy)-ethyl]-amine or its alkali or earth alkali metal salt are specific examples of the novel compounds.

The compounds obtained according to the invention are especially well suited for use in alkaline aqueous solutions, such as detergents and cleaning agents. Furthermore, the compounds are suited for use in photography chemicals.

The compounds as obtained are useful chelators in, for example, alkaline aqueous solutions of hydrogen peroxide or in alkaline or acidic solutions of peroxy compounds such as peracetic acid. The compounds are particularly useful as chelators of transition metals in a pretreatment before the bleaching of cellulose with ozone, hydrogen peroxide or peroxy acids such as performic, peracetic, perpropionic or Caro's acid and combinations of the same.

The compounds are usable chelators of earth alkali metals from alkaline water solutions. This ability makes them useful in detergent applications.

Since the compounds as obtained do not contain phosphorus and contain very little nitrogen, they load the environment considerably less than do the chelators currently used.

Specific uses covered by the invention are defined in claims 14–18.

The invention is described below with the help of examples. However, these examples do not limit the invention.

EXAMPLE 1

A maleic acid solution was prepared by dissolving 56.0 g (0.571 mol) of maleic anhydride in 124.3 ml of water. 116.2 g of this solution was added to 71.3 g of a 48% lye solution (0.856 mol NaOH). During the addition the temperature of the reaction mixture was maintained at 70–90° C. Lanthanum(III)oxide, $La_2O_3$, (15.5 g, 0,048 mol) was dissolved in remaining maleic acid solution ( 64.1 g, 0.192 mol) and added to the reaction mixture together with diethanolamine (20.0 g, 0.190 mol). The reaction mixture was stirred at 95° C. under a reflux condenser for 24 hours. The reaction mixture was rendered acidic (pH 3.5) by addition of oxalic acid, $C_2O_4H_2 \cdot 2H_2O$ (47.96 g in 71.90 ml of water, 0.380 mol) and stirred at 80° C. for 1 hour. The reaction mixture was cooled and the formed La(III) oxalate precipitate was removed by filtration. From the remaining solution (194.1 g), which contained water 75.2%, the organic compounds were analyzed by means of $^{13}C$ NMR spectra. BCEEAA and BCEEA were identified from the $^{13}C$ NMR spectra. Unreacted initial substances were identified on the basis of reference spectra: diethanolamine and maleic acid, as well as oxalic acid used for the precipitation of the catalyst. Malic acid and fumaric acid were formed as byproducts of the reaction; these were also identified on the basis of reference spectra.

On the basis of a quantitative $^{13}$C NMR analysis, the composition of the obtained reaction mixture containing BCEEAA and BCEEA, was as follows:

| | |
|---|---|
| BCEEAA | 13.61 w-% |
| BCEEA | 3.99 w-% |
| diethanolamine | 2.39 w-% |
| maleic acid | 2.00 w-% |
| malic acid | 1.79 w-% |
| water | 75.20 w-% |

Since BCEEA and BCEEAA and the derivatives thereof are poorly soluble in organic solvents, the $^1$H-NMR technique cannot be used for the analysis of the reaction mixture. $^{13}$C NMR spectroscopy is therefore a useful method for the analysis of the reaction mixture. The $^{13}$C NMR spectrum data for BCEEAA and BCEEA are shown in Table 1, entries 1 and 2.

The NMR analysis was confirmed by analyzing the same reaction mixture as silyl or methyl ester derivatives by gas chromatograph combined with mass spectrometer (GC-MS). The mass spectral data of the silyl derivatives of BCEEAA and BCEEA are shown in table 2, entries 1 and 2.

EXAMPLE 2

The reaction product from reaction 1 was refluxed for 2 hours and the reaction mixture was cooled. A sample was withdrawn for analysis. The cyclic product A was identified by $^{13}$C NMR and by GC-MS analysis (table 1, entry 5 and table 2, entry 5, respectively). The reaction mixture was rendered basic (pH 13) by addition of 48% sodium hydroxide solution and stirred at 102° C. for 2 h and cooled to room temperature. Quantitative $^{13}$C analysis revealed the composition of the reaction mixture to be:

| | |
|---|---|
| BCEEA | 6.23 w-% |
| diethanolamine | 0.95 w-% |
| maleic acid | 0.51 w-% |
| malic acid | 0.92 w-% |
| fumaric acid | 0.99 w-% |
| oxydibutanedioate | 0.64 w-% |
| water | 89.76 w-% |

EXAMPLE 3

A disodium maleate solution was prepared by dissolving 19.6 g (0.2 mol) of maleic anhydride in 50 ml of water and by adding the resulting maleic acid solution to 33.3 g of a 48% lye solution (0.4 mol NaOH). During the addition the temperature of the reaction mixture was maintained at 70–90° C. Lanthanum(III)oxide, La$_2$O$_3$, (8.15 g, 0.025 mol) was dissolved in 65% nitric acid (16.8 g, 0.173 mol) and in 12 ml of water and added to the reaction mixture together with N-methyl diethanol-amine (11.9 g, 0.1 mol). The reaction mixture was stirred at 85° C. under a reflux condenser for 70 hours. The reaction mixture was cooled and rendered acidic (pH 1-2) by addition of sulfuric acid. The formed La(III)sulfate precipitate was removed by filtration. The remaining sodium sulfate was precipitated by addition of acetone. After filtration and concentration the remaining solution (7.2 g), which contained water 67.6 w-%, the organic compounds were analyzed as silyl or methyl ester derivatives by means of $^{13}$C NMR spectra and by GC-MS (table 1, entry 3, and table 2, entry 3, respectively).

On the basis of a quantitative $^{13}$C NMR analysis, the composition of the obtained reaction mixture was as follows:

| | |
|---|---|
| N-methyl-BCEEA | 12.4 w-% |
| N-methyl-diethanolamine | 9.9 w-% |
| maleic acid, fumaric acid | 0.7 w-% |
| malic acid | 2.5 w-% |
| oxydibutanedioate | 6.9 w-% |
| water | 67.6 w-% |

EXAMPLE 4

Diethanolamine (10 g, 0.095 mol) was treated with chloroacetic acid (9.44 g, 0.100 mol) in 10 g of water. During the addition the temperature raised to 57° C. Sodium hydroxide (49% solution in water, 8.15 g, 0.100 mol) was added to the reaction mixture and the temperature of the reaction mixture was elevated to 100° C. for 10 minutes and cooled to room temperature. The N-methylcarboxy diethanol-amine (MCDEA) was identified from $^{13}$C NMR and GC-MC spectra (table 1, entry 6, and table 2, entry 6, respectively).

EXAMPLE 5

Lanthanum oxide (6.07 g, 0,09 mol), water (20 ml), and maleic anhydride (9.13 g, 0.093 mol) was added to the reaction vessel and the solution was heated to 85° C. Sodium hydroxide solution (49%, 7.60 g, 0.093 mol) and water (23 g) was added to the reaction mixture. MCDEA (38% solution in water, 20 g 0.047 mol), the reaction product from the carboxymethylation reaction described in example 4, was added into the reaction mixture. The pH of the resulting suspension was adjusted to pH 8.5 by addition of sodium hydroxide solution. The resulting solution was stirred at 100° C. for 48 h. The lanthanum catalyst was precipitated by addition of oxalic acid. The reaction product was identified by using $^{13}$C NMR and GC-MS spectra (table 1, entry 4, and table 2, entry 4). $^{13}$C NMR analysis revealed the composition of the reaction mixture to contain:

| | |
|---|---|
| N-carboxymethyl-BCEEA | 23.86 w-% |
| N-carboxymethyl-N-[1,2-dicarboxyethoxy)-ethyl]-N-ethanolamine | 6.42 w-% |
| malic acid | 2.09 w-% |

EXAMPLE 6

The reaction product described in example 2, containing BCEEA, was stirred with a magnesium salt of 2-bromoacetic acid with the excess of magnesium oxide at 35° C. for 3 days. The reaction product CMBCEEA was identified from $^{13}$C NMR spectra of the product by comparison with the previously obtained spectra (Table 1, entry 4).

EXAMPLE 7

Stabilization of peracetic acid (PAA) is essential in pulp bleaching liquors and in detergent solutions. In the presence of metal ions (for example Mn, Fe, Cu), PAA is decomposed rapidly and the bleaching efficiency is decreased.

The efficiency of the novel chelating agents in stabilizing peracetic acid solutions were tested as follows:

A water solution containing Mn ions 0.4 mg/l, was prepared by addition of Mn sulphate to water. An appropriate amount of DTPA, MeBCEEA and CMBCEEA, respectively, were added to the solution in order to adjust the concentration of the chelating agent to 140 mg/l. The pH of the solution was adjusted to 4,5 by using sodium hydroxide and the solution was warmed up to 50° C. Peracetic acid concentration was adjusted to 2,0 g/l by addition of distilled, 36% PAA solution.

The decomposition of PAA in the solutions was followed by iodometric titration. The titration results are shown in table 3.

TABLE 3

Stability of peracetic acid solutions containing chelating agents as stabilizers at 50° C. in the presence of Fe and Mn ions.

| | Concentration of peracetic acid (g/l) | | |
|---|---|---|---|
| Sample | 1 | 2 | 3 |
| Stabilizer | DTPA | MeBCEEA | CMBCEEA |
| Storage time (min) | | | |
| 0 | 2.10 | 2.06 | 2.00 |
| 15 | 0.36 | 1.96 | 1.95 |
| 30 | 0.35 | 1.98 | 1.95 |
| 45 | 0.34 | 1.96 | 1.98 |
| 60 | 0.33 | 1.94 | 2.00 |
| 273 | | 1.90 | |
| 300 | | | 1.82 |

The results of the above mentioned example show clearly the usefullness of the novel complexing agents as stabilizers of peracetic acid solutions.

EXAMPLE 8

The efficacy of the novel chelating agents to bind calcium ions was tested by using the method of Blay and Ryland (Analytical letters 4(10), pp. 653–663 (1971). Thus, 0.002 M solution of calcium chloride ($CaCl_2$) buffered to pH 9.5 was titrated by a buffered solution of the chelating agent. During the titration, the non-chelated calcium ions were determined by using a calcium selective electrode. Known chelating agents, DTPA, EDTA and nitrilotriacetic acid (NTA) were used as references.

TABLE 4

| | Non-chelated Ca (mol-%) | | | |
|---|---|---|---|---|
| Sample | 1 | 2 | 3 | 4 |
| Chelating agent | DTPA | EDTA | NTA | MeBCEEA |
| Molar equivalents of chelating agent added | | | | |
| 0.0 | 100.0 | 100.0 | 100.0 | 100.0 |
| 6.7 | 84.9 | 67.4 | 84.9 | 72.8 |
| 13.3 | 72.3 | 61.9 | 61.9 | 61.9 |
| 20.0 | 61.6 | 52.8 | 61.6 | 48.9 |
| 26.7 | 52.7 | 48.8 | 52.7 | 41.8 |
| 33.3 | 45.3 | 45.3 | 48.9 | 35.9 |
| 40.0 | 42.1 | 39.0 | 45.5 | 28.6 |
| 46.7 | 36.4 | 36.4 | 42.4 | 22.9 |
| 53.3 | 29.2 | 39.7 | 39.7 | 19.8 |
| 60.0 | 25.4 | 34.6 | 34.6 | 14.8 |
| 66.7 | 19.0 | 25.9 | 30.3 | 11.1 |

TABLE 4-continued

| | Non-chelated Ca (mol-%) | | | |
|---|---|---|---|---|
| Sample | 1 | 2 | 3 | 4 |
| 73.3 | 14.4 | 21.1 | 26.6 | 7.7 |
| 80.0 | 10.1 | 17.3 | 23.5 | 5.4 |
| 86.7 | 6.1 | 12.2 | 17.9 | 3.8 |
| 93.3 | 2.3 | 6.4 | 13.8 | 2.9 |
| 100.0 | 2.0 | 6.0 | 12.0 | 2.5 |

The results shown in table 4 show clearly that N-methyl BCEEA binds calcium ions more effectively than the reference chemicals.

EXAMPLE 9

An O-Q-Op (oxygen delignification, chelation, peroxide reinforced oxygen) delignified softwood kraft pulp (kappa number 3.6, viscosity 718 $dm^3$/kg) sample was taken from a Finnish pulp mill. 100 grams pulp samples were treated in laboratory with peracetic acid solutions and bleached with alkaline hydrogen peroxide. The bleaching conditions and chemical dosages are shown in table 5. The bleaching trials were conducted in plastic bags.

As can be seen from table 5, the concentration of residual peracetic acid (PAA) after treatment in the solution containing MeBCEEA or CMBCEEA is higher than in the PAA solution containing DTPA as chelating agent. This results in a lower consumption of peracetic acid in the bleaching. It is of importance especially if the liquor is recycled. The treatment of the pulp with the PAA solution containing MeBCEEA results in similar final viscosity as the treatment with the PAA solution containing DTPA. When no chelating agent was used, the final viscosity of the bleached pulp was unacceptable. In addition, the brightness of the pulp is much better after treatment with the PAA solution containing MeBCEEA. The treatment of the Pulp with the PAA solution containing CMBCEEA gives an improved viscosity and a better brightness than the treatment of the pulp with similar solution containing DTPA. According to these test results, it is clear that the use of the new chelating agents is advantageous in bleaching of pulp in sequences which comprise the use of peroxygen chemicals such as hydrogen peroxide, peroxy acids, etc.

TABLE 5

| Delignifying and bleaching of chemical pulp | | | | |
|---|---|---|---|---|
| | QPAA | QPAA | QPAA | QPAA |
| t, min | 120 | 120 | 120 | 120 |
| T, ° C. | 70 | 70 | 70 | 70 |
| Cs, % | 10 | 10 | 10 | 10 |
| Start pH | 5.4 | 5.5 | 5.3 | 5.6 |
| End pH | 4.6 | 4.3 | 4.6 | 4.6 |
| PAA, kg/tm | 12 | 12 | 12 | 12 |
| Chelating agent | no | DTPA | MeBCEEA | CMBCEEA |
| Dosage kg/tm | — | 2 | 2 | 2 |
| Residual PAA, kg/tm | 4.6 | 0.6 | 4.3 | 3.4 |
| Residual $H_2O_2$, kg/tm | 0.7 | 0.9 | 1.1 | 1.1 |
| Kappa | 2.6 | 3.1 | 2.6 | 2.5 |
| Viscosity, $dm^3$/kg | 707 | 681 | 702 | 719 |
| Brightness % ISO | 74.9 | 72.1 | 74.2 | 74.3 |
| | ↓ | ↓ | ↓ | ↓ |
| | P | P | P | P |

TABLE 5-continued

Delignifying and bleaching of chemical pulp

| | | | | |
|---|---|---|---|---|
| t, min | 180 | 180 | 180 | 180 |
| T,C | 90 | 90 | 90 | 90 |
| Cs, % | 10 | 10 | 10 | 10 |
| Start pH | 10.4 | 10.4 | 10.4 | 10.4 |
| End pH | 10.4 | 10.2 | 10.3 | 10.3 |
| H$_2$O$_2$, kg/tm | 20 | 20 | 20 | 20 |
| NaOH, kg/tm | 15 | 10 | 12 | 10 |
| Residual H$_2$O$_2$, kg/tm | 4 | 9.1 | 9.8 | 12.8 |
| H$_2$O$_2$ consumption, kg/tm | 16.0 | 10.9 | 10.2 | 7.2 |
| Residual NaOH, kg/tm | 5.1 | 5.2 | 6.3 | 6.3 |
| Kappa | 1.3 | 1.9 | 1.5 | 1.5 |
| Viscosity, dm$^3$/kg | 489 | 570 | 577 | 643 |
| Δ-Viscosity, % | 31.9 | 20.6 | 19.6 | 10.4 |
| Brightness % ISO | 87.2 | 84.6 | 86.6 | 86.4 |
| Δ-brightness % ISO | 22.8 | 20.2 | 22.2 | 22.0 |
| Yellowness | 6.7 | 11.3 | 9.3 | 9.7 |

TABLE 1

| Formula | $^{13}$C NMR PPM (explanation) |
|---|---|
| 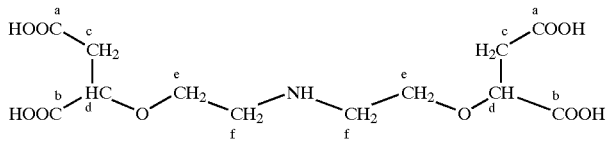<br>BCEEA | 175 (a), 176 (b), 37.9 (c), 75.8 (d), 66.4 (e), 47.8 (f) |
| 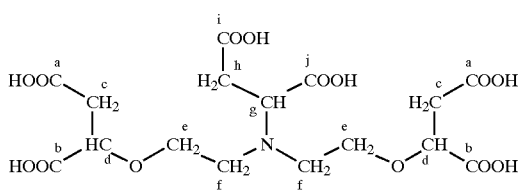<br>BCEEAA | 175 (a), 176 (b), 37.9 (c), 75.8 (d), 65.5 (e), 54.4 (f), 62.0 (g), 32.6 (h), 170.3 (I), 173.9 (j) |
| 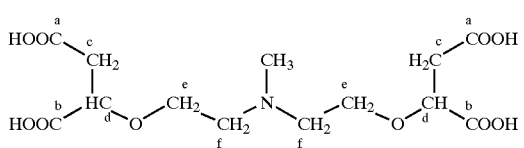<br>MeBCEEA | 175.9 (a), 176.0 (b), 37.5 (c), 75.5 (d), 63.7 (e), 55.2 (f), 40.4 (g) |
| 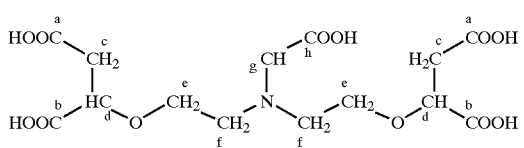<br>CMBCEEA | 176.8 (a), 177.3 (b), 39.9 (c), 77.8 (d), 66.9 (e), 56.7 (f), 58.1 (g), 172.2 (h) |
| 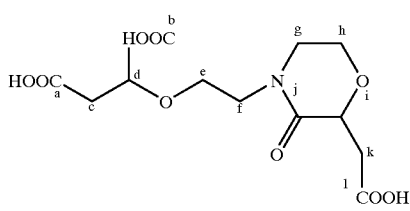<br>Compound A | 177.6 (a), 178.1 (b), 40.3 (c), 77.9 (d), 65.3 (e), 50.3 (f), 49.6 (g), 70.8 (h), 76.3 (i), 172.8 (j), 39.6 (k), 177.0 (l) |
| 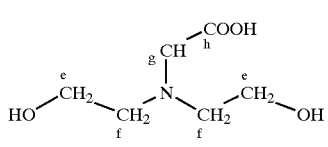 | 62.6 (e), 57.5 (f), 58.8 (g), 175.3 (h) |

TABLE 2

Mass spectra of the silyl derivatives of the novel compounds

| Compound | MS- spectra of the silylated compounds m/z (relative intensity) |
|---|---|
| BCEEA | 406 (100%), 73 (96%), 333 (50%), 407 (34%), 147 (17%), 171 (16%), 422 (10%), 245 (8%) |
| BCEEAA | 73 (100%), 594 (61%), 147 (32%), 245 (18%), 610 (15%), 678 (12%), 608 (9%), 520 (5%) |
| MeBCEEA | 348 (100%), 73 (54%), 349 (28%), 364 (18%), 147 (15%), 245 (10%), 624 (2%), 522 (1%) |
| CMBCEEA | 73 (100%), 464 (94%), 75 (36%), 465 (35%), 147 (31%), 245 (18%), 638 (15%), 117 (12%) |
| Compound A | 73 (100%), 258 (65%), 75 (63%), 184 (38%), 147 (30%), 245 (26%), 140 (24%), 274 (24%) |

What is claimed is:

1. A method for the preparation of an N-bis-(2-(1,2-dicarboxy-ethoxy)-ethyl)-amine derivative having the formula (I)

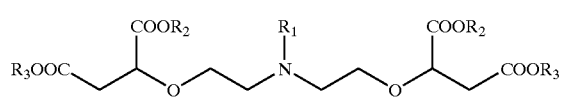

characterized in that an alkali or earth alkali metal salt of maleic acid is brought to a reaction with an N-substituted diethanolamine with a substituent group $R_1$, to react with the two ethanol groups of said diethanolamine while the substituent group $R_1$ bound to the N atom is unreactive with said maleic acid salt and thus preserved in the derivative obtained as the final product, wherein $R_1$ is an alkyl chain with a single carboxylic acid group, and $R_2$ and $R_3$ are hydrogen or alkali or earth alkali metal ions.

2. A method according to claim 1, wherein the substituent group is a carboxymethyl group, the reaction yielding N-carboxymethyl-bis-(2-(1,2-dicarboxy-ethoxy)-ethyl)-amine or an alkali or earth alkali metal salt thereof as the final product.

3. A method for the preparation of N-bis-(2-(1,2-dicarboxy-ethoxy)-ethyl)-amine derivative having the formula (I)

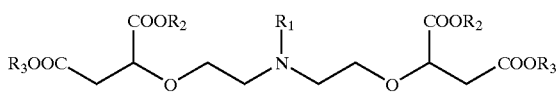

said method comprising the steps of reacting diethanolamine with an alkali metal salt of maleic acid in basic conditions to yield N-bis-(2-(1,2-dicarboxy-ethoxy)-ethyl)-amine and N-bis-[2-(1,2-dicarboxy-ethoxy)-ethyl]-aspartic acid, causing the mixture to be turned acidic and then once more basic, thereby turning any N-bis-(2-(1,2-dicarboxy-ethoxy)-ethyl)-aspartic acid formed as an intermediate product at said first step to N-bis-(2-(1,2-dicarboxy-ethoxy)-ethyl)-amine, reacting the N-bis-(2-(1,2-dicarboxy-ethoxy)-ethyl)-amine with a substitution reagent replacing the hydrogen bound to the N atom with said group $R_1$ to obtain the product of Formula I, wherein $R_1$ is a group comprising an alkyl chain with a single carboxylic acid group and the alkyl group does not contain a plurality of carboxylic acid groups, and $R_2$ and $R_3$ are hydrogen or alkali or earth alkali metal ions.

4. A method according to claim 3, wherein at the first reaction step a lanthanide compound, a mixture of lanthanide compounds or an earth alkali metal compound is used as a catalyst.

5. A method according to claim 3 or 4, wherein the final substitution step is carried out with an organic halide or anhydride substituting an organic group for the hydrogen atom.

6. A method according to claim 5, wherein the substitution step is carried out with 2-bromoacetic acid or 2-chloroacetic acid as the reagent, the method yielding N-carboxymethyl-N-bis-(2-(1,2-dicarboxy-ethoxy)-ethyl)-amine or an alkali or earth alkali metal salt thereof as the final product.

7. An N-bis-(2-(1,2-dicarboxy-ethoxy)-ethyl)-amine derivative, wherein the derivative has the formula (I)

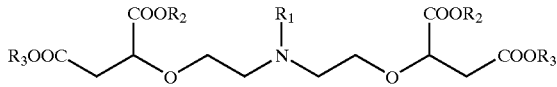

wherein $R_1$ is a group consisting of an alkyl chain with a single carboxylic acid group wherein the alkyl group does not contain a plurality of carboxylic acid groups, and $R_2$ and $R_3$ represent hydrogen or alkali or earth alkali metal ions.

8. A derivative according to claim 7, wherein it is N-carboxy-methyl-N-bis-(2-(1,2-dicarboxy-ethoxy)-ethyl)-amine or its alkali or earth alkali metal salt.

9. A method of chelating metals in a metal(s)-containing fluid in a chemical application, said method comprising contacting the metal(s)-containing fluid with a N-bis-[2-(1, 2-dicarboxy-ethoxy)-ethyl]-amine derivative of claim 7 in an amount sufficient to chelate metals(s).

10. The method of claim 9, wherein the fluid is a bleach containing hydrogen peroxide or a peracid and wherein the chemical application is bleaching chemical or mechanical pulp.

11. The method of claim 9, wherein the fluid is a bleach and wherein the chemical application is bleaching textiles.

12. The method of claim 9, wherein the metal is calcium.

13. The method of claim 9, wherein the metal(s)-containing fluid is a detergent solution, a disinfecting solution, a cleaning agent, or a mixture thereof.

14. The method of claim 9, wherein the metal(s)-containing fluid is a photography composition.

15. The method of claim 9, wherein the N-bis-(2-(1,2-dicarboxy-ethoxy)-ethy)-amine derivative is N-carboxy-methyl-N-bis-(2-(1,2-dicarboxy-ethoxy)-ethyl)-amine.

16. A method for the preparation of N-bis-(2-(1,2-dicarboxy-ethoxy)-ethyl)-amine derivative having the formula (II)

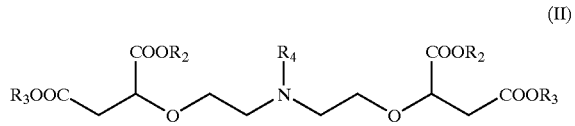

said method comprising the steps of reacting diethanolamine with an alkali metal salt of maleic acid in basic conditions to yield N-bis-(2-(1,2-dicarboxy-ethoxy)-ethyl)-amine and N-bis-2-(1,2-dicarboxy-ethoxy)-ethyl)-aspartic acid, causing the mixture to be turned acidic and then once more basic, thereby turning any N-bis-(2-(1,2-dicarboxy-ethoxy)-ethyl)-aspartic acid formed as an intermediate product at said first step to N-bis-(2-(1,2-dicarboxy-ethoxy)-ethyl)-amine, reacting the N-bis-(2-(1,2-dicarboxy-ethoxy)-ethyl-amine with a substitution agent replacing the hydrogen bound to the N atom with said group $R_4$ to obtain the product of Formula II, wherein $R_4$ substituted on the nitrogen is a C1–C30 alkyl, a C1–C30 alkyl with between 1 and about 10 carboxylic acid groups attached thereon, a C1–C30 alkyl with between 1 and about 10 carboxylic acid ester groups attached thereon, a polyethoxylated hydrocarbon chain containing between 1 and about 20 ethoxy groups, a carboxylic acid amide containing from 1 to about 30 carbon atoms where the N—$R_4$ bond is an amide bond, an N-alkyl-N-bis-(2-(1,2-dicarboxy-ethoxy)-ethyl)-amine containing from 1 to about 20 carbon atoms in the alkyl chain, or alkali or alkaline earth metal salts of any of these, and $R_2$ and $R_3$ are hydrogen or alkali or earth alkali metal ions.

17. The method of claim 16 wherein reacting the substituted or unsubstituted maleic acid with diethanolamine to form an intermediate is performed in the presence of a catalyst comprising one or more of calcium oxide, calcium hydroxide, calcium carbonate, magnesium oxide, magnesium hydroxide, magnesium carbonate, nickel compounds, and rare earth compounds.

18. The method of claim 17 wherein the catalyst is a rare earth compound comprising lanthanum(III) maleate, lanthanum(III) nitrate, lanthanum(III) chloride, lanthanum oxide, and/or lanthanum octanoate.

19. The method of claim 17 wherein the catalyst comprises lanthanum compounds, praseodymium compounds, or neodymium compounds, the method further comprising adding to the product a mineral acid or organic acid and a molar excess of oxalic acid to form a precipitate of the rare earth metal, and separating the precipitate from the product.

20. The method of claim 17 further comprising adding a molar excess of carbonate to the product to form rare earth carbonate precipitates, the method further comprising separating the precipitate from the product.

21. The method of claim 17 wherein the substituting agent comprises a carboxylic acid halide, a carboxylic acid anhydride, a methoxyalcoxyl halide, an alkyl halide, or a mixture thereof.

22. The method for the preparation of N-bis-(2-(1,2-dicarboxy-ethoxy)-ethyl)-amine derivative of claim 16 wherein $R_4$ is a C1–C30 alkyl.

23. The method for the preparation of N-bis-(2-(1,2-dicarboxy-ethoxy)-ethyl)-amine derivative of claim 16 wherein $R_4$ is a C1–C30 alkyl with between 1 and about 10 carboxylic acid groups attached thereon, or alkali or alkaline earth metal salts thereof.

24. The method for the preparation of N-bis2-(1,2-dicarboxy-ethoxy)-ethyl)-amine derivative of claim 16 wherein $R_4$ is a C1–C30 alkyl with between 1 and about 10 carboxylic acid ester groups attached thereon, or alkali or alkaline earth metal salts thereof.

25. The method for the preparation of N-bis-(2-(1,2-dicarboxy-ethoxy)-ethyl)-amine derivative of claim 16 wherein $R_4$ is a polyethoxylated hydrocarbon chain containing between 1 and about 20 ethoxy groups, or alkali or alkaline earth metal salts thereof.

26. The method for the preparation of N-bis-(2-(1,2-dicarboxy-ethoxy)-ethyl)-amine derivative of claim 16 wherein $R_4$ is a carboxylic acid amide containing from 1 to about 30 carbon atoms where the N—$R_4$ bond is an amide bond, or alkali or alkaline earth metal salts thereof.

27. The method for the preparation of N-bis-(2-(1,2-dicarboxy-ethoxy)-ethyl)-amine derivative of claim 16 wherein $R_4$ is an N-alkyl-N-bis-(2-(1,2-dicarboxy-ethoxy)-ethyl)-amine containing from 1 to about 20 carbon atoms in the alkyl chain, or alkali or alkaline earth metal salts thereof.

28. The method for the preparation of N-bis-(2-(1,2-carboxy-ethoxy)-ethyl)-amine derivative of claim 16 wherein $R_4$ is an (CH2)n—COOR, where n=1–20 and R=alkyl, alkali or earth alkali metal.

29. A method for the preparation of an N-bis-(2-(1,2-dicarboxy-ethoxy)-ethyl)-amine derivative having the formula (III)

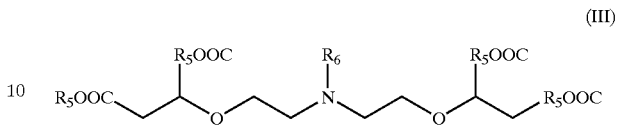

(III)

characterized in that an alkali or earth alkali metal salt of maleic acid is brought to a reaction with an N-substituted diethanolamine with a substituent group $R_6$, to react with the two ethanol groups of said diethanolamine while the substituent group $R_6$ bound to the N atom is unreactive with said maleic acid salt and thus preserved in the derivative obtained as the final product, wherein $R_6$ is an alkyl chain containing 1 to 30 carbon atoms or an alkyl chain containing 1 to 30 carbon atoms with a carboxylic acid group substituted thereon, and the $R_5$ groups are independently hydrogen, alkyl containing 1 to 30 carbon atoms, or alkali or earth alkali metal ions.

* * * * *